(12) United States Patent
Shin

(10) Patent No.: US 6,891,089 B2
(45) Date of Patent: May 10, 2005

(54) GRASS CULTIVAR NAMED 'BENEST 1' AND 'DONGRAE KORYOGI'-SPECIFIC STS MARKER

(75) Inventor: Hong-Kyun Shin, Gunpo (KR)

(73) Assignee: Samsung Everland Co., Ltd., Gunpo (KR)

( * ) Notice: Subject to any disclaimer, the term of this patent is extended or adjusted under 35 U.S.C. 154(b) by 149 days.

(21) Appl. No.: 10/157,245

(22) Filed: May 30, 2002

(65) Prior Publication Data

US 2004/0003439 A1 Jan. 1, 2004

(51) Int. Cl.⁷ .................................................. A01H 5/00
(52) U.S. Cl. ...................................................... 800/320
(58) Field of Search .......................................... 800/320

Primary Examiner—Anne Marie Grunberg
Assistant Examiner—Annette H Para
(74) Attorney, Agent, or Firm—Birch, Stewart, Kolasch & Birch, LLP

(57) ABSTRACT

Disclosed is a new and distinct variety of Zoysia grass, named 'Benest 1', and a 'Dongrae Koryogi'-specific STS marker. 'Benest 1' of the present invention is prepared by mating two zoysia grasses, 'Anyang Chunggi' with excellent resistance to disease and cold and 'Dongrae Koryogi' with good texture. The 'Dongrae Koryogi'-specific STS marker of the present invention is developed by adding extra bases to a 'Dongrae Koryogi'-specific operon primer, OPD12 and the nucleoic acid sequence of a 'Dongrae Koryogi'-specific DNA fragment obtained by PCR using the OPD12 primer, and is extremely useful for identification of cultivar of hybrid species of 'Dongrae Koryogi'.

2 Claims, 7 Drawing Sheets

[NOTE]

M : DNA size marker
lane 1 : Anyang Chunggi
lane 2 : Dongrae Koryogi
Arrow : Specific band

FIG. 3

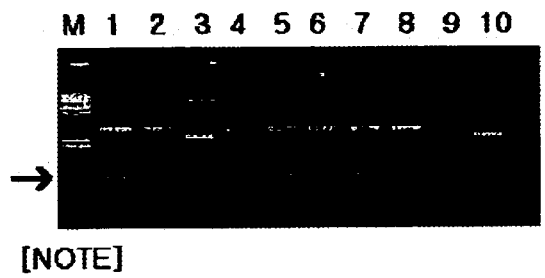

[NOTE]

M : λ /DNA digested with Hind III
lane 1~10 : recombinant clone

FIG. 4

```
  1 CACCGTATCC CCAGGAAAGT TGGAACCAAG AAGTGAAAGG TTGCTCTTCA TATTGTGGGT  60
 61 CATGACGATG AACCCGAAGA GCCACAGGAG ATCAACATGG TTTTAGCTAA GCCTCTAGAT 120
121 CATGAGAGAG GCAGAGTGCA CTGACTATAT ATGGAATGCA TCAACAGCAA TTGTGAGAAG 180
181 AGGAGATAAT TGCTATTCTA AGGACAAGCA ATGCATTGAA ACTAAGTTTT GGAGTTTCTT 240
241 TCATGCAGAT TATTACAACT TAGTGTACGT GGTGATGAAG AATCTAATTA TTGAGATGCA 300
301 GTGGACGGAT TAGGAATACA TGGCCAAGAA GAACAATGCA GTATTCAATG AAGTTATTGA 360
361 GGCTTGCACA TATCATGGGA TTAAGGACAT CTTAGATTTC AAGTATCCAT GGAATAAAGC 420
421 AGTTATCGCT CAGTTCTATG CCACTATCTA TTATCATCAG AAAAGAGAGG CCAAGATTTC 480
481 TTGGATGACA GGTTCAGACG TCTACTCAGT CACAGTGAGA CGCTTTGCCA ATATTATAAA 540
541 GTTCCGCAGC GGTTTCTCCA ATGAGGCCAG AAATCACAAT AAGCTAGTGC TTGATGTCAA 600
601 TGCTATGAAT TTCATGTATG AAACCTCCCT CACATTTCTC TACACCAAAC CCTACTGGGT 660
661 TCCTTCCCTT CTATATTTTT GGCTCCATAA AAGTTCTGTA CAGTATACTT CTAGTTGACT 720
721 AATAAACAAA TGACAGGTAT TTAACACAAA ATTATTCTTG ATAATCATAG CACTTTCGGT 780
781 ACCATTTTCA TTGTCCAAGA TCACACGGTC AGCACATGTA CTCCGTCCAA CGGATAATAA 840
841 CCATGTAATG ACTTGAAAGT ATTTTAGTTC AATTGACTCA CCAGGTTTGC ACAGCGATGC 900
901 ATGTGGCGGC TGGTAGTAGC ATTCTAGATG ATAAGGTTGA TCATGCAGGATACGGTG      937
```

[NOTE]

M : λ DNA digested with Hind III
lane 1 : Dongrae Koryogi
lane 2 : Anyang Chunggi
lane 3 : Korea oommon
lane 4 : Meyer
lane 5 : Zenith
lane 6 : Seoul Ilban
lane 7: S-94

FIG. 6

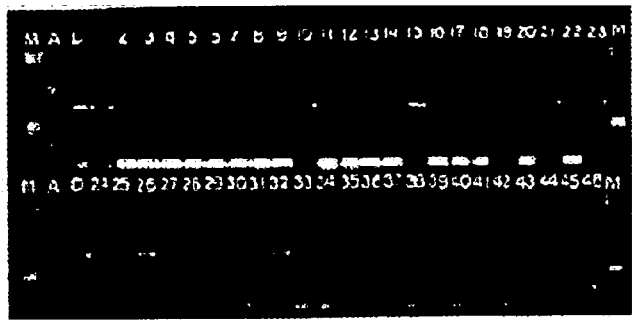

[Note]
M: λ DNA digested with Hind III, A: Anyang Chunggi, D: Dongrae Koryogi

| | | |
|---|---|---|
| lane 1: 98AM-03 | lane 17: 98AM-24 | lane 33: 98AM-43 |
| lane 2: 98AM-04 | lane 18: 98AM-26 | lane 34: 98AM-44 |
| lane 3: 98AM-05 | lane 19: 98AM-28 | lane 35: 98AM-45 |
| lane 4: 98AM-06 | lane 20: 98AM-30 | lane 36: 98AM-46 |
| lane 5: 98AM-08 | lane 21: 98AM-31 | lane 37: 98AM-47 |
| lane 6: 98AM-10 | lane 22: 98AM-32 | lane 38: 98AM-48 |
| lane 7: 98AM-11 | lane 23: 98AM-33 | lane 39: 98AM-49 |
| lane 8: 98AM-12 | lane 24: 98AM-34 | lane 40: 98AM-50 |
| lane 9: 98AM-14 | lane 25: 98AM-35 | lane 41: 98AM-53 |
| lane 10: 98AM-15 | lane 26: 98AM-36 | lane 42: 98AM-54 |
| lane 11: 98AM-17 | lane 27: 98AM-37 | lane 43: 98AM-57 |
| lane 12: 98AM-18 | lane 28: 98AM-38 | lane 44: 98AM-58 |
| lane 13: 98AM-19 | lane 29: 98AM-39 | lane 45: 98AM-59 |
| lane 14: 98AM-21 | lane 30: 98AM-40 | lane 46: 98AM-60 |
| lane 15: 98AM-22 | lane 31: 98AM-41 | |
| lane 16: 98AM-23 | lane 32: 98AM-42 | |

FIG. 7

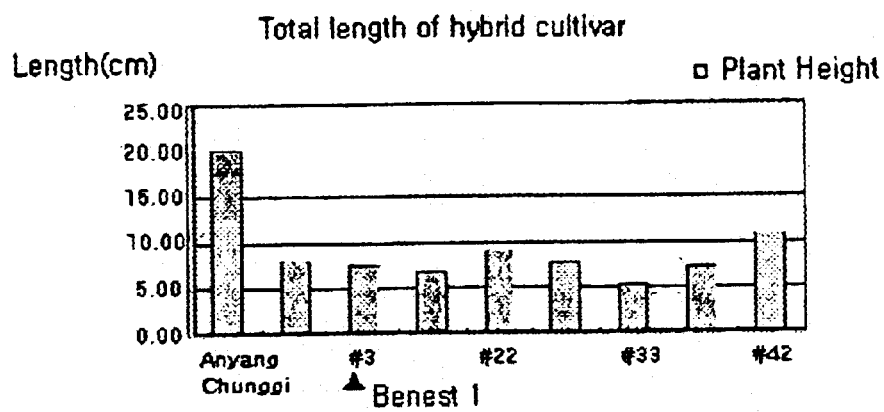

GRASS CULTIVAR NAMED 'BENEST 1' AND 'DONGRAE KORYOGI'-SPECIFIC STS MARKER

TECHNICAL FIELD

The present invention relates to a novel cultivar of zoysia grass named 'Benest 1' (hereinafter, referred to as 'Benest 1') and a 'Dongrae Koryogi'-specific Sequence Tagged Site (STS) marker for identification of mating cultivars of 'Dongrae Koryogi' zoysia grass. More particularly, the present invention relates to 'Benest 1' having merits of both 'Anyang Chunggi' zoysia grass having excellent disease resistance and cold resistance, and 'Dongrae Koryogi' zoysia grass with good leaf texture, which is prepared by mating the two zoysia grasses using 'Dongrae Koryogi' as a pollen parent, and a 'Dongrae Koryogi'-specific STS marker being capable of analyzing success of mating and cultivar of hybrids of 'Dongrae Koryogi' zoysia grass, which is prepared by adding extra bases to an operon primer specific for 'Dongrae Koryogi', the extra bases being selected from a nucleic acid sequence of 'Dongrae Koryogi'-specific DNA fragment, which is obtained by PCR using the operon primer.

BACKGROUND ART

Zoysia grass, which is a perennial herb, belongs to Graminae family, and propagates by stolons and rhizomes, showing wide variation in its morphology and other characteristics, according to regions. It has been reported that there are, in Korea, five or six species of zoysia grasses including *Z. japonica, Z. matrella, Z. tenufolia, Z. sinica* and *Z. macrostachya*. Zoysia grass, as a warm-season grass, widely grows wild in Far Eastern Asia including Korea, and is used in almost all places including gardens, parks, sports grounds, golf links, banks of roads, reclaimed lands, and airports. Especially, zoysia grass is well suited to Korean climate, and is superior in its adaptability to various environments to cool-season grasses and other warm-season grasses. In addition, zoysia grass is known to have strong resistances to drought, trampling, cold, heat, and salt. However, zoysia grass, commonly, has problems that its propagation is relatively slow and is green for a short period of time. In this regard, there is a need for development of cultivars of zoysia grass.

In Korea, 63 excellent grass species were selected from zoysia grasses collected from natural populations since 1965 in Korea, performed by D. Y. You and D. E. Yeam of Seoul National University. Thereafter, it was reported that *Z. koreana* of acinus form has rapid breeding and salt resistance properties, as disclosed by D. E. Yeam, Y. G. Joo, I. S. Han, et. al. who participated in the Zoysia germplasm resource investigation conducted by the USDA (United States Department of Agriculture) in 1982 (Yeam, et. al., 1986; Kim, 1989). However, between 1985 and 1994, there was almost no research on breeding of zoysia grasses in Korea, and from 1995, several universities and research institutes in Korea including Konkuk University, Dankook University, Turfgrass and Environment Research Institute of Samsung Everland Inc. began carrying out research on zoysia grasses obtained from Seoul National University. Although Korea is the home of zoysia grass herbs, utilization and development of novel cultivars of zoysia grass lags behind the USA or Japan.

With the announcement of United Nations Convention on Biological Diversity in 1992, a major content provision of which protects property right of innate seeds of individual nation, each nation of world has started to recognize the importance of its own genetic resources, resulting in that it will become gradually more difficult to export or distribute valuable genetic resources as well as genetic resources of which properties are unknown.

Among the zoysia grasses described above, *Z. japonica* is, in Korea, mainly used in golf links, sports grounds, or parks, and *Z. matrella* is partly used in warm regions of Korea. In spite of the wide uses of grass, in Korea, there is no systematic selection and breeding of cultivars of zoysia grass. Moreover, some advanced countries, such as the USA or Japan, have collected grasses naturally growing in Korea and other Southeast Asian countries, bred them, and selected excellent cultivars to sell them to other countries, resulting in their occupying a dominant position in international market. In contrast, especially in Korea, randomly selected and propagated zoysia grasses have been circulated, causing non-uniformity in the view that various species of grass are mingled without classification of species. In addition, the grasses produced in advanced countries are now market at a low cost. Therefore, it is urgently required to collect zoysia grasses with excellent genotypes and growth habit, and propagate zoysia grasses having excellent morphological and genotypic characteristics.

DISCLOSURE OF THE INVENTION

Accordingly, it is an object of the present invention to provide a new cultivar of zoysia grass having excellent morphological and genotypic characteristics by mating 'Anyang Chunggi' zoysia grass having excellent disease resistance and cold resistance with 'Dongrae Koryogi' zoysia grass, having fine texture.

It is another object of the present invention to provide a 'Dongrae Koryogi'-specific DNA fragement and its nucleic acid sequence, wherein the 'Dongrae Koryogi'-specific DNA fragement is prepared by performing PCR using a selected operon primer capable of specifically amplifying a portion of 'Dongrae Koryogi' genomic DNA.

It is a further object of the present invention to provide a 'Dongrae Koryogi'-specific STS marker, which is prepared by adding more bases specific for 'Dongrae Koryogi' to a selected operon primer to identify cultivar of hybrid species of 'Dongrae Koryogi'.

To achieve the objects described above, in accordance with an aspect of the present invention, there are provided hybrid cultivars prepared by pollinating pistils of 'Anyang Chunggi' zoysia grass with pollen of 'Dongrae Koryogi' zoysia grass.

In accordance with another aspect of the present invention, in order to select cultivars of hybrid species of 'Dongrae Koryogi', there is provided a 'Dongrae Koryogi'-specific DNA fragment, which is prepared by a RAPD analysis using genomic DNA of 'Anyang Chunggi' and 'Dongrae Koryogi' and an operon primer OPD12, and an STS marker capable of identify cultivars of the hybrids and other grasses circulating in the market, which is prepared by addition of 12 bases to the OPD12 primer, where the sequence consisting of 12 bases is selected from a full nucleic acid sequence of the 'Dongrae Koryogi'-specific DNA fragment.

BRIEF DESCRIPTION OF THE DRAWING

The above and other objects, features and other advantages of the present invention will be more clearly understood from the following detailed description taken in conjunction with the accompanying drawings, in which:

FIG. 3 is a photograph showing a digestion pattern of cloning vectors, which may carry a DNA fragment amplified from 'Dongrae Koryogi' genomic DNA, using an operon primer OPD12;

FIG. 4 is a full sequence (SEQ ID NO:1) of a DNA fragment amplified from 'Dongrae Koryogi' genomic DNA using an OPD12 primer, which is represented by the two underlined sequences;

FIG. 6 is a photograph showing an agarose gel electrophoresis pattern of PCR products of hybrid species of zoysia grass using an STS marker;

FIG. 7 is a graph showing heights of 'Benest 1' of the present invention, 'Anyang Chunggi', and other hybrid species;

BEST MODES FOR CARRYING OUT THE INVENTION

Figure 1:
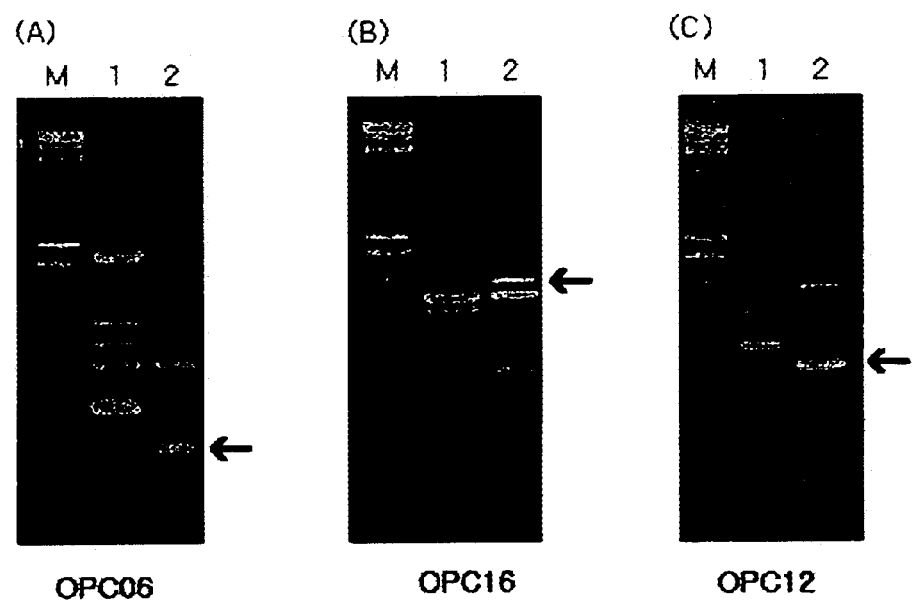
FIG. 1 is a photograph showing an agarose gel electrophoresis pattern of randomly amplified polymorphic DNA (RAPD) of 'Anyang Chunggi' and 'Dongrae Koryogi' zoysia grasses using Dongrae Koryogi-specific operon primers, OPC06, OPC16, and OPD12.

The present invention was conceived in order to breed a novel variety of grass with merits of 'Anyang Chunggi' zoysia grass that has excellent resistance to disease and cold, and 'Dongrae Koryogi' zoysia grass, having a fine texture. Breeding of grasses was mainly carried out using a selective breeding method, but in the present invention, a mating breeding method was used to breed grasses with specific characteristics.

'Anyang Chunggi' zoysia grass, as a new grass species collected by B. C. Lee, the former president of Samsung Corporation, Korea, was patented with Korean Pat. AM 277113, and in Korea, was widely utilized in golf course fairways and tee boxes, and other landscaped areas. 'Anyang Chunggi', with a leaf width of 3–4 mm, has characteristics of Z. sinica, shows intermediate characteristics between Z. japonica and Z. matrella, and grows vertically rather than in a creeping manner. 'Dongrae Koryogi' zoysia grass belongs to Z. matrelia family found in fairways of Dongrae Benest Golf Club, Korea, and has a good texture with a narrow leaf of 2–3 mm, but it perishes during winter.

According to the present invention, pistils of 'Anyang Chunggi', used as a mother plant, were pollinated with pollen of 'Dongrae Koryogi', used as a pollen parent, to produce hybrid species. After mating, 46 individuals, expected to be hybrid species, were obtained by performing a procedure comprising collection, sowing, and sprouting of fruiting seeds.

In order to identify successful mating of the 46 individuals, OPC06, OPC16 and OPD12 primers, as operon primers specific for 'Dongrae Koryogi', were primarily selected among forty operon primers, which are random primers, by RAPD analysis, performed by PCR using the operon primers and genomic DNA of 'Anyang Chunggi' or 'Dongrae Koryogi' as a template. Then, with the three operon primers, PCR analysis was performed on the 46 potential hybrids, identifying a DNA fragment of about 900 bp in size, designated 'D12-900', was amplified in a PCR reaction mixture only with OPD12 primer.

With an aim to increase specificity of the OPD12 primer for 'Dongrae Koryogi', the OPD12 primer was modified through introduction of 12 more bases of a certain nucleic acid sequence, located at 5' or 3' ends of the 'D12-900', generating an STS marker comprising D12F primer (SEQ ID NO: 2) and D12R primer (SEQ ID NO: 3).

In accordance with the present invention, it was confirmed that the STS marker is highly specific for 'Dongrae Koryogi', but not to other grass varieties including 'Anyang Chunggi', 'Meyer', and 'Zenith'. On the whole, the STS marker is a 'Dongrae Koryogi'-specific STS marker. Moreover, the 'Dongrae Koryogi'-specific STS marker of the present invention can be usefully applied for identification of cultivars of hybrids of 'Dongrae Koryogi' and 'Dongrae Koryogi' grasses circulating in the market.

Among seven hybrid species, defined by RAPD analysis with the OPD12 primer and the 'Dongrae Koryogi'-specific STS marker, a hybrid having excellent characteristics was selected as a new grass cultivar of the present invention, named 'Benest 1'.

'Benest 1' of the present invention is characterized by dark green leaf color, high density, and fine texture, and it asexually propagates by stolons and rhizomes.

The present invention will be explained in more detail with reference to the following examples in conjunction with the accompanying drawings. However, the following examples are provided only to illustrate the present invention, and the present invention is not limited to them.

EXAMPLE 1

Production of a New Grass Cultivar by Mating 'Anyang Chunggi' and 'Dongrae Koryogi' Zoysia Grasses 'Anyang Chunggi' was used as a mother plant, and 'Dongrae Koryogi' as a pollen parent.

Step 1: Preparation of Zoysia Grasses for Mating

Two sods of zoysia grasses, 'Anyang Chunggi' and 'Dongrae Koryogi', were prepared by cutting work using a hole cutter of 11.5 cm in diameter, and planted in plastic pots with an inner diameter of 16.5 cm. 'Anyang Chunggi' was planted at the end of February 1998, and 'Dongrae Koryogi' in November 1997, and the two planted zoysia grasses were then maintained in a greenhouse of 5° C. for the winter season. In order that the two grass cultivars come into flower at the same time, 'Dongrae Koryogi', of which formation of flower stalk is more rapid than that of 'Anyang Chunggi', was maintained in the greenhouse for the period from March to April after being grown at the outside of the greenhouse for a certain period.

Step 2: Mating of 'Anyang Chunggi' and 'Dongrae Koryogi'

With 'Anyang Chunggi' as a mother plant and 'Dongrae Koryogi' as a pollen parent, mating was performed from early morning to evening for a period from Apr. 10 to May 10, 1998 by pollinating pistils of 'Anyang Chunggi' with collected pollen of 'Dongrae Koryogi'. After the pollens turned brown in color, stamens generated in 'Anyang Chunggi' were removed from 'Anyang Chunggi', thus preventing self-fertilization.

With the consideration that flower stalks from 'Dongrae Koryogi' are typically formed earlier than 'Dongrae Koryogi', part of 'Dongrae Koryogi' surviving the winter was moved to the outside of the greenhouse early in March. The rest, in the greenhouse, began to develop flower stalks from March 10. 'Dongrae Koryogi' grasses moved to the outside of the greenhouse were then divided to two groups, which were placed into the greenhouse on March 23 and March 30, respectively, but flower stalks from them were formed at a far more late time than an expectative time even with a pretty low number because of cold weather of about one week during the maintenance at the outside of the greenhouse. However, 'Dongrae Koryogi' continuously grown in the greenhouse maintained their flowers for over one month, allowing for harvesting of pollen from them and mating.

From April 5, 'Anyang Chunggi' cultivar started to form flower stalks. Accordingly, mating was carried out from April 10.

Step 3:Seed Harvesting After Mating

After two months, from June 4 to June 17, fruiting seeds were harvested.

802 Seeds were harvested from a total of 57 flower stalks. It was found that 515 of harvested seeds were mature seeds, and 287 were sterile.

TABLE 1

Seed harvesting from hybrid cultivars through mating of 'Anyang Chunggi' and 'Dongrae Koryogi'

| Total flower stalks | Average seeds per flower stalk | Total seeds | Sterile seeds | Mature seeds |
|---|---|---|---|---|
| 57 | 19 | 802 | 287 | 515 |

Step 4:Treatment of Seeds and Seeding

The harvested seeds were wrapped with gauze, and then treated with a solution of 25% KOH containing one drop of Tween-20 for 30 minutes. The seeds were washed with running water for 24 hours, sown in petri dishes, and maintained at 30° C. for three days, allowing for sprouting. The sprouted seeds were transferred to soil and grown in a greenhouse. It was found that the sprouting rate of hybrid seeds was about 60%.

Hybrid plants were cultivated in a greenhouse for a seedling period. However, a large number of seedlings died due to rust and leaf blight because rainy weather continued through the seedling period, resulting in only 70 individuals surviving. The viable 70 individuals were allowed to pass the winter season in the planted form in experimental packs. As will be described below, DNA analysis was performed on the surviving 46 individuals during the winter season.

EXAMPLE 2

Selection of 'Dongrae Koryogi'-Specific RAPD Primer Marker

With an aim of detecting whether the surviving 46 individuals prepared in Example 1, expected to be hybrids of 'Anyang Chunggi' and 'Dongrae Koryogi', were hybrids or not, a 'Dongrae Koryogi'-specific RAPD primer, which will be used as a marker, was primarily selected.

Because 'Dongrae Koryogi' zoysia grass was used as a pollen parent, once hybrids are established, the resulting hybrids have 'Dongrae Koryogi'-specific markers. Accordingly, in order to investigate whether mating occurred or not, markers specifically amplified in 'Dongrae Koryogi' should be selected. A 'Dongrae Koryogi'-specific marker was picked according to the below procedure.

Step 1:Selection of 'Dongrae Koryogi'-Specific Marker

To select 'Dongrae Koryogi'-specific markers, randomly amplified polymorphic DNA (RAPD) analysis was performed using 40 operon primers including OPC06, which are random primers.

DNA extraction from the two zoysia grasses, 'Anyang Chunggi' and 'Dongrae Koryogi', was carried out, as follows: 2 g of leaves were collected from the two zoysia grasses grown in experimental packs, and ground with liquid nitrogen. 150 $\mu$l aliquots of the ground leaves were transferred into 1.5 ml microtubes, and then mixed well with 750 $\mu$l of an extraction solution preheated to 60° C., which contains in a proportion of 5:5:2 a DNA extraction buffer (0.35 M sorbitol, 0.1 M Tris-base, 5 mM EDTA, pH 7.5), a nucleus lysis buffer (0.2 M Tris-base, 0.05 M EDTA, 2 M NaCl, 2% CTAB), and 5% sarkosyl, and then heated to 60° C. for 30 minutes. The mixture was supplemented with 500 $\mu$l of chloroform, followed by gently mixing for 15 minutes (min). Thereafter, the mixture was centrifuged at 10,000 rpm for 10 min, and the DNA was precipitated by an adding equal volume of isopropyl alcohol. The precipitated DNA was recovered by centrifugation at 10,000 rpm for 10 min, washed twice with 70% ethanol, and then resuspended in TE buffer. DNA amount of each sample was determined using a fluorometer, and the extracted DNA was used as a template in the following PCR reaction.

There were prepared PCR reaction mixtures of 20 $\mu$l containing 20 ng of a template, 100 $\mu$M of dNTP, 0.2 $\mu$M of operon primer, 10× reaction buffer, and 1.5 mM of $Mg^{2+}$. With the use of a PCR machine, Perkin Elmer 9600, the PCR reaction mixture was preincubated for 3 min at 94° C., and PCR was performed for 45 cycles in which each cycle was composed of 1 min at 94° C., 1 min at 35° C., and 2 min at 72° C., followed by incubation for 10 min at 72° C.

PCR products were separated in a 1.4% agarose gel for 4 hours under a condition of 100 V, and then stained with EtBr and visualized under a UV illuminator.

Figure 2:
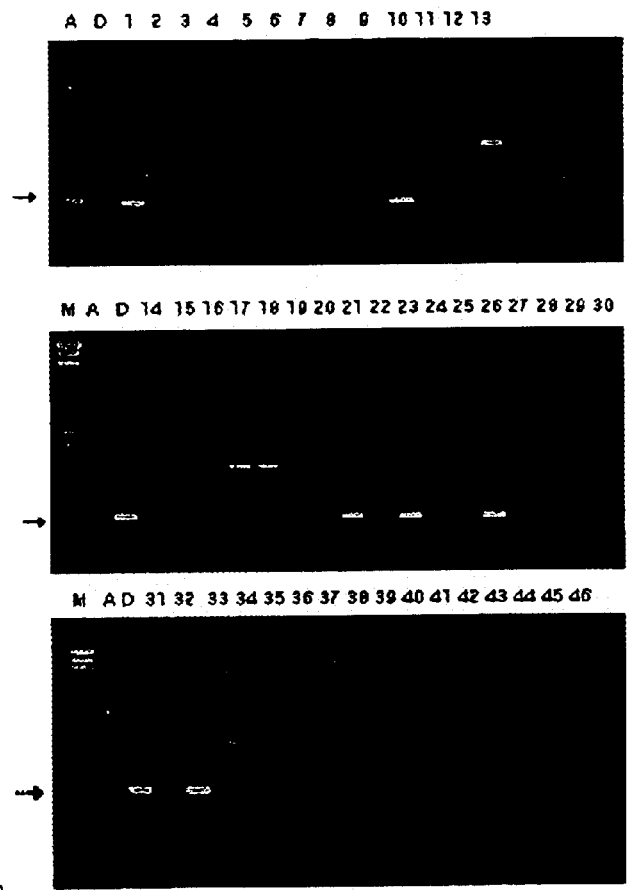
FIG. 2 is a photograph showing results of mating test using an operon primer, OPD12, for plants expected to be $F_1$ hybrids.

In PCR reactions using OPC06, OPC16, and OPD12 primers among 40 operon primers, it was detected that a 'Dongrae Koryogi'-specific band in each case was amplified with a different molecular weight (refer to FIG. 1). However, when PCR was performed using the genomic DNA extracted from the 46 individuals prepared in Example 1, PCR products amplified with OPC06 and OPC16 primers did not show 'Dongrae Koryogi'-specific bands, while there was detected a DNA fragment of about 900 bp in PCR products using OPD12 primer (refer to FIG. 2), thus proving that OPC06 and OPC16 primers were not useful for analysis for hybrid cultivars. Using OPD12 primer, the above DNA fragment of about 900 bp, specifically amplified in 'Dongrae Koryogi' zoysia grass, was called 'D12-900'.

In the RAPD analysis of the 46 individuals, prepared in Example 1, using OPD12 primer, 'Dongrae Koryogi'-specific bands were observed in seven individuals including hybrid AM3, AM15, AM22, AM31, AM33, AM36, and AM42.

Step 2: Confirmation of 'Dongrae Koryogi'-specific Marker by RAPD Analysis

In order to develop DNA markers capable of distinguishing 'Dongrae Koryogi' zoysia grass from other cultivars, comparative zoysia grasses including 'S-94' developed by Seedkorea co., ltd., Korea, 'Seoul illban' as a Korean common variety, 'Meyer', 'Zenith', 'Yaggi' as a common variety of Z. japonica in Korea, and 'Anyang Chunggi' were used. DNA preparation and RAPD analysis through PCR using OPD12 primer were carried out according to the procedures described above to determine whether D12–900 band is specific to 'Dongrae Koryogi' or not. As a result, D12–900 band was found to be amplified only in 'Dongrae Koryogi'.

EXAMPLE 3

Determination of Nucleic acid Sequence of 'Dongrae Koryogi'-Specific Marker and Development of STS Marker Since RAPD analysis is typically accomplished by PCR in which an annealing reaction of primers is carried out using short primers with a relatively low Tm value, primers are liable to non-specifically bind to a denatured template, resulting in different PCR products being produced according to reaction conditions. To overcome this problem, in the present invention, through analysis of the nucleic acid sequence of a RAPD marker, there was accomplished the synthesis for a longer primer than the primarily used random primer, allowing for high specificity upon being used in PCR. In the present invention, the longer and highly specific primer called 'STS (Sequence Tagged Site) marker'. A 'Dongrae Koryogi'-specific STS marker was prepared according to the following steps.

Step 1:Selection, Cloning and Nucleic Acid Sequence Determination of 'Dongrae Koryogi'-Specific Marker Then, clones 2 and 7 were used for nucleic acid sequence analysis performed by a Sanger chain termination method, in which the sequencing was conducted in both forward and reverse directions, confirming that clones 2 and 7 carry the same insert (refer to FIG. 4).

Step 2:Conversion of 'Dongrae Koryogi'-Specific RAPD Marker to STS Marker

Based on the nucleic acid sequence of 'Dongrae Koryogi'-specific DNA fragment, 12 bases were added to the random primer, OPD12, giving a primer pair, D12F and D12R. As used herein, 'F' and 'R' indicate forward and reverse, respectively. The sequences of the primers, D12F and D 12R, are given in Table 2.

Figure 5:
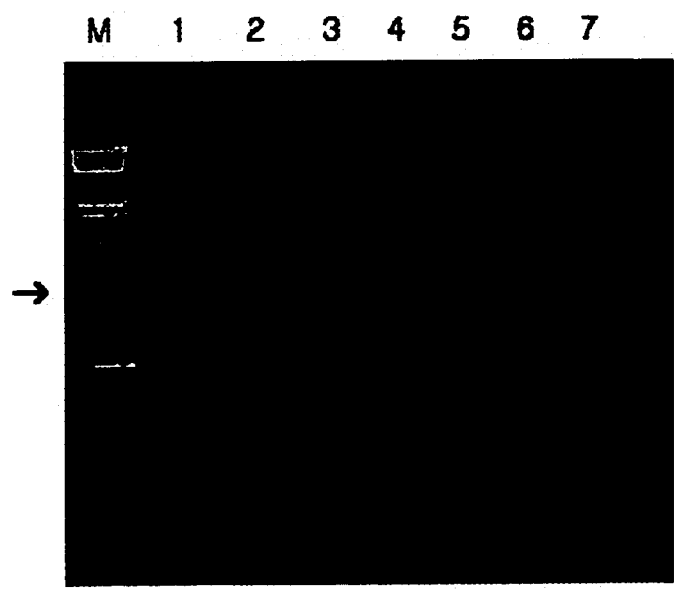
FIG. 5 is a photograph showing an agarose gel electrophoresis pattern of PCR products of zoysia grasses including 'Dongrae Koryogi' using an STS marker.

An annealing temperature for PCR was determined by calculating Tm values of the newly synthesized longer primers. Using D12F and D12R primers, PCR was performed with genomic DNA from 'Dongrae Koryogi', 'Anyang Chunggi', 'Seoul illban', 'Meyer', 'Zenith', 'Yaggi', or 'S-94'. There were prepared PCR reaction mixtures of 25 μl containing 50 ng of a template, 200 μM of dNTP, 25 pmol of each primer, 100 mM Tris-HCl (pH 8.3), 1.25 mM of $MgCl_2$, and 50 mM KCl. The PCR reaction mixture was preincubated for 3 min at 94° C., then 35 cycles in which each cycle was 1 min at 94° C., 1 min at 66° C., and 2 min at 72° C., followed by incubation for 10 min at 72° C. As a result, a specific DNA fragment was detected only in 'Dongrae Koryogi', not in other varieties (refer to FIG. 5), demonstrating that the primer set, D12F and D12R, can be used as a 'Dongrae Koryogi'-specific marker. Accordingly, such a modified STS marker can be used for analysis of cultivar of hybrids.

TABLE 2

| RAPD marker name | Primer name of STS marker | Sequence (5'→3') | Tm (° C.), 4(G + C) + 2(A + T) |
|---|---|---|---|
| D12-900 | D12F | CACCGTATCCCCAGGAAAGTTG (SEQ ID NO: 2) | 68 |
| | D12R | CACCGTATCCTGCATGATCAAC (SEQ ID NO: 3) | 66 |

A 'Dongrae Koryogi'-specific DNA fragment of about 900 bp in size was obtained from an RAPD analysis using an OPD12 primer, and extracted from an agarose gel using a DNA elution kit (QIAGEN, USA). After the extraction of the DNA fragment was confirmed on an agarose gel and its amount was determined, for cloning of the DNA fragment into a pGEM-T easy vector (Promega, USA), a ligation reaction was carried out for 24 hours at 14° C. with a mixture of the DNA fragment and the vector in a proportion of 3:1. Then, the reaction mixture was introduced into E. coli DH10B strain by an electroporation method, and the E. coli DH10B cells were smeared onto a solid medium containing 50 μg/mL ampicillin, X-Gal, and IPTG, and incubated for 16 hours at 37° C. to form colonies. After picking white colonies expected to be recombinants, plasmid DNA was isolated using an alkaline lysis method. To investigate insertion of Dongrae Koryogi-specific DNA fragment, plasmid DNA was digested by EcoRI for 2 hours at 37° C., and electrophoresed in an agarose gel of 1.4%. Eight recombinant clones were obtained. As shown in FIG. 3, it was found that, as a result of digestion of EcoRi, size of inserts corresponded to that of the above Dongrae Koryogi-specific DNA fragment, where an arrow indicates the insert of about 900 bp.

Step 3:Analysis for Hybrid Species of 'Anyang Chunggi' and 'Dongrae Koryogi'

With genomic DNA from hybrids of 'Anyang Chunggi' and 'Dongrae Koryogi', PCR was performed using the STS marker comprising D12F and D12R. The same result as in PCR using an operon primer, OPD12, was observed. That is, STS marker was detected in hybrids, AM 3, AM 15, AM 22, AM 31, AM 33, AM 36, and AM 46. Therefore, the STS maker can be used as a marker capable of distinguishing cultivars of the hybrids as well as commercially available grasses.

EXAMLE 4

Analysis for Growth Habit of the Hybrid Cultivars Between 'Anyang Chunggi' and 'Dongrae Koryogi'

In order for registration of the hybrid individuals (herein, also called hybrid species or cultivars) of Anyang Chunggi' and 'Dongrae Koryogi' as a new cultivar, growth habit and morphological properties were investigated. It was found that most of the hybrid cultivars had intermediate characteristics between 'Anyang Chunggi' and 'Dongrae Koryogi'. That is, most of the hybrids had narrower leaf width than 'Anyang Chunggi', and similar leaf color to 'Anyang Chunggi' or slightly darker leaf color than 'Anyang Chunggi', and their total length (plant height) was shorter than 'Anyang Chunggi' and longer than 'Dongrae Koryogi'.

Comparison of total length of the hybrid cultivars with 'Anyang Chunggi' and 'Dongrae Koryogi' is given in FIG. 7, showing that the hybrids are, in total length, intermediate between 'Anyang Chunggi' and 'Dongrae Koryogi'. It was observed that total length was gradually reduced in an order of 'Anyang Chunggi'>AM 42>AM 22>'Dongrae Koryogi'>AM 31>AM 03>AM 36>AM 15>AM 33. Moreover, the hybrid individuals were found to have a shorter total length than conventional available cultivars, such as 'S-94', 'Seoul illban', and 'Meyer', reducing mowing frequency of lawn grass. In addition, in golf links, the hybrid cultivars have a good ability to support golf balls thanks to their upright form.

Figure 8:
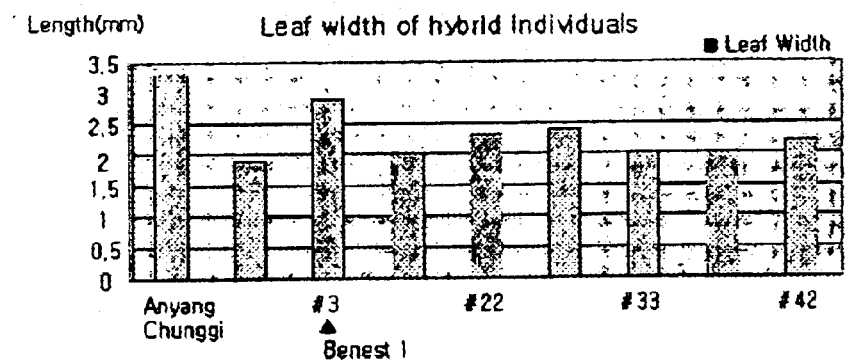
FIG. 8 is a graph showing leaf widths of 'Benest 1' of the present invention, 'Anyang Chunggi', and other hybrid species.

Comparison of leaf width of the hybrid individuals with 'Anyang Chunggi' and 'Dongrae Koryogi' is given in FIG. 8, where the hybrid cultivars were observed to have intermediate leaf widths between 'Anyang Chunggi' and 'Dongrae Koryogi'. Leaf width was gradually reduced in the order of 'Anyang Chunggi'>AM 03>AM 31>AM 22>AM 42>AMs 15, 33, 36>'Dongrae Koryogi'. Hybrid species showed slightly wider leaf width than 'Dongrae Koryogi', but narrower leaf width than 'Anyang Chunggi'. Moreover, leaf width of the hybrids was found to be narrower than other grasses having intermediate characteristics between Z. japonica and Z. matrella. Accordingly, the hybrid cultivars have a good leaf texture.

Figure 9:
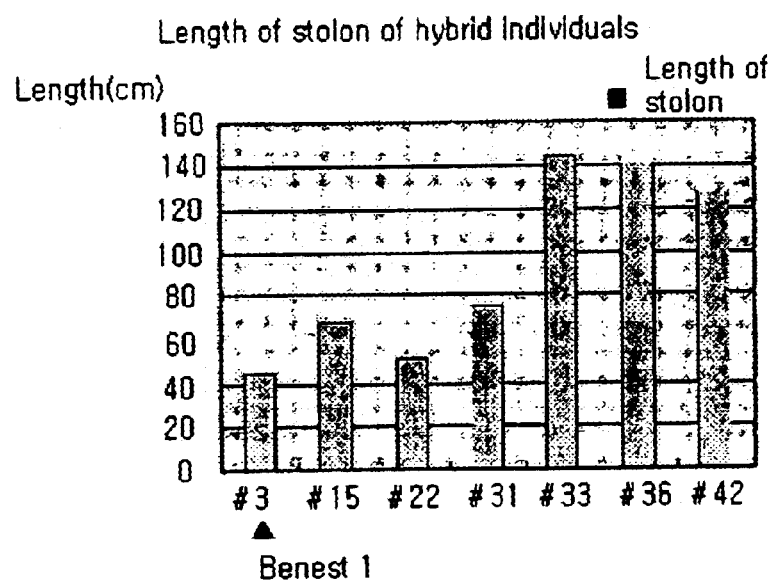
FIG. 9 is a graph showing lengths of stolons of 'Benest 1' of the present invention, 'Anyang Chunggi', and other hybrid species.

Lengths of stolons of the hybrid individuals are presented in FIG. 9. Length of stolon determines the time required for recovering a specific area. That is, grass cultivar with long stolons can recover more rapidly than one with relatively short stolons. It was found that the hybrid individuals have stolons of over 40 cm in length, with an order of AM 33>AM 36>AM 42>AM 31>AM 15>AM 22>AM 03. Especially, it was found that AM 33 hybrid has the longest stolons of over 140 cm in length as well as a relatively high average number of stolons of 3.2±1.3. Also, a stolon of 200 cm in length was observed in a hybrid AM 42. Moreover, grass variety having stolons of over 100 cm in length is very suitable for areas requiring anti-erosion work and rapid recovering.

TABLE 3

Physical characteristics of hybrid cultivars of 'Anyang Chunggi' and 'Dongrae Koryogi'

| Hybrid cultivars | Physical characteristics | | | |
|---|---|---|---|---|
| | Leaf width (mm) | Leaf length (cm) | Stolon length (cm) | Other characteristics |
| AM 3 | 2.9 ± 0.1 | 7.4 ± 1.8 | 44.8 ± 3.3 | Dark green leaf color, high density, soft texture |
| AM 15 | 2.0 ± 0.1 | 6.7 ± 0.6 | 68.7 ± 15 | Low plant height, narrow leaf, hard texture |
| AM 22 | 2.3 ± 0.2 | 9.1 ± 1.0 | 50.5 ± 13.3 | Rapid growth, lower plant height than 'Anyang Chunggi' |
| AM 31 | 2.4 ± 0.1 | 7.7 ± 1.3 | 75.7 ± 20.6 | Rapid recovering rate, rapid growth |
| AM 33 | 2.0 ± 0.0 | 5.2 ± 1.5 | 144.0 ± 13.0 | Rapid recovering rate, rapid growth |
| AM 36 | 2.0 ± 0.1 | 7.1 ± 1.5 | 140.7 ± 41.3 | Rapid recovering rate, very long stolon |
| AM 42 | 2.2 ± 0.3 | 10.6 ± 2.4 | 126.8 ± 36.7 | Rapid recovering rate |

Figure 10:
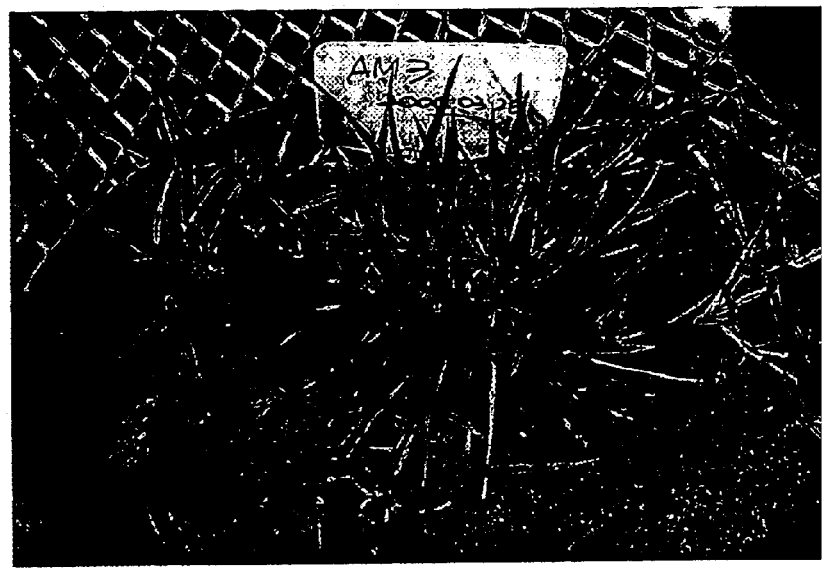
FIG. 10 is a photograph showing morphological characteristics of 'Benest 1' of the present invention, growing in a pot.

Of the hybrid cultivars, a hybrid AM03, characterized by leaf width of 2.9±0.1 mm, leaf length of 7.4±1.8 cm, stolon length of 44.8±3.3 cm, dark green leaf color, high density, and soft texture, was designated as 'Benest 1', a new cultivar of grass of the present invention. A photograph of 'Benest 1' grown in a pot is provided in FIG. 10.

EXAMPLE 5

Asexual Propagation Method of 'Benest 1'

Typically, zoysia grass propagates by stolons and rhizomes with a very high recovering ability. Rhizomes, as a horizontally spreading subterranean stems, produce a bud at each node, which grow to a shoot. From the shoot, an aerial stem is produced. Also, each node in subterranean stem takes root. Like rhizomes, stolons, which are horizontal stems above ground, produce a shoot and roots in each node. 'Benest 1', a new hybrid cultivar of 'Anyang Chunggi' and 'Dongrae Koryogi' zoysia grasses, spreads by stolons and rhizomes, allowing for tight growth.

A new grass cultivar 'Benest 1' of the present invention was asexually propagated according to procedures described in the following Experimental Examples.

EXPERIMENTAL EXAMPLE 1

Propagation by Sprigging

As used herein, 'sprig' refers to a portion of a grass plant having stolons or rhizomes. Sprigs were prepared by cutting a portion including nodes from a new cultivar 'Benest 1' of the present invention, and planted at a depth of 2–3 inches at an interval of 6–12 inches. Sufficient water was supplied under carefully controlled condition, and shoots and roots were produced from each node, finally establishing a lawn grass.

EXPERIMENTAL EXAMPLE 2

Propagation by Stolonizing

A portion of 'Benest 1' grass plant including stolons or rhizomes was prepared by cutting, and broadcast spreading was performed on an area for stolonizing, followed by soil covering and watering to prevent drying. In this method, much more grasses are required than in the sprigging method.

EXPERIMENTAL EXAMPLE 3

Propagation by Sodding

Flat square grass sods prepared from 'Benest 1' of the present invention, which is 2–6 feets in length and 1–1.5 feets in width, were planted at a constant interval, and spaces among the grass sods were covered by spreading of stolons and rhizomes, giving a lawn grass.

EXPERIMENTAL EXAMPLE 4

Propagation Method by Plugging

Plug means a small cylinder- or block-shaped piece. Grass plugs from 'Benest 1' of the present invention were planted at a constant interval, and spaces among the grass plugs were covered by spreading of stolons and rhizomes, establishing a lawn grass.

EXPERIMENTAL EXAMPLE 5

Propagation by Multishoot

Highly divided tissues, such as shoot apex, or nodes of stolons or rhizomes, were collected from 'Benest 1' of the present invention, disinfected, and planted in an MS (Murashige & Skoog) medium containing 0.1–1.0 mg/L of BA (6-benzyladenin) and 0.05–0.1 mg/L of NAA (1-naphthaleneacetic acid) to induce multishoots. Emerged multishoots were separated from each other, and the separated individuals were transferred to a two times-diluted MS medium, which did not contain any hormone, to take root. Rooted plants were acclimated and then cultivated in a greenhouse, allowing for propagation.

TABLE 4

| Composition of MS medium | |
|---|---|
| Constituent | Conc. (mg/L) |
| Macronutrients | |
| $KNO_3$ | 1900 |
| $NH_4NO_3$ | 1650 |
| $MgSO_4 \cdot 7H_2O$ | 370 |
| $KH_2PO_4$ | 170 |
| $CaCl_2 \cdot 2H_2O$ | 440 |
| Micronutrients | |
| $H_3BO_3$ | 6.2 |
| $MnSO_4 \cdot 4H_2O$ | 22.3 |
| $ZnSO_4 \cdot 7H_2O$ | 8.6 |
| $NaMoO_4 \cdot 2H_2O$ | 0.25 |
| $CuSO_4 \cdot 5H_2O$ | 0.025 |
| $CoCl_2 \cdot 6H_2O$ | 0.025 |
| KI | 0.83 |
| $FeSO_4 \cdot 7H_2O$ | 27.8 |
| Disodium EDTA | 37.3 |
| Glysine | 2 |
| Sucrose | 30 × 103 |

TABLE 4-continued

| Composition of MS medium | |
|---|---|
| Constituent | Conc. (mg/L) |
| Vitamins | |
| Thiamine hydrochloride | 0.5 |
| Pyridoxine hydrochloride | 0.5 |
| Nicotinic acid | 0.5 |
| Myo-inositol | 100 |
| pH | 5.7 |

EXPERIMENTAL EXAMPLE 6

Propagation by Redivision of Plants From Callus

From 'Benest 1' of the present invention, highly divided tissues, such as node of stolons or rhizomes, immature inflorescence, immature embryo, shoot apex, or root, were collected, disinfected, and planted in a MS (Murashige & Skoog) medium additionally containing 1–5 mg/L of 2,4-D (2,4-dichlorophenoxyacetic acid) and 0.5–1.0 mg/L of kinetin (refer to Table 4) to induce calluses. The calluses were transferred to a two times-diluted MS medium, which did not contain any hormone, for redivision. Redivided plants were acclimated and then cultivated in a greenhouse, allowing for propagation.

INDUSTRIAL APPLICABILITY

As described in the above Examples, the present invention provides a new grass cultivar 'Benest 1' having merits of both zoysia grasses, 'Anyang Chunggi' with excellent resistance to disease and cold and 'Dongrae Koryogi' with good texture, which can be obtained by mating the two zoysia grasses. According to the present invention, successful mating of hybrids between the two zoysia grasses species was confirmed through an RAPD analysis using a 'Dongrae Koryogi'-specific STS marker comprising D12F and D12R primers, obtained from combination of a random operon primer OPD 12 and a nucleic acid sequence of a 'Dongrae Koryogi'-specific DNA fragment amplified using the OPD 12 primer. A specific DNA fragment amplified by PCR using the STS marker was demonstrated to reside only in 'Dongrae Koryogi' and the hybrids including 'Benest 1', not in other zoysia grasses species. Therefore, the 'Dongrae Koryogi'-specific STS marker of the present invention is very useful for identification of hybrid cultivars derived from 'Dongrae Koryogi' and commercially circulating 'Dongrae Koryogi' species.

What is claimed is:

1. A 'Dongrae Koryogi'-specific DNA marker designated 'D12-900' (SEQ ID NO:1) capable of identifying cultivars of hybrids of 'Dongrae Koryogi' zoysia grass, which is obtained from genomic DNA of 'Dongrae Koryogi' by PCR using an operon primer OPD12.

2. A 'Dongrae Koryogi'-specific STS marker comprising D12F primer (SEQ ID NO: 2) and D12R primer (SEQ ID NO:3), which are oligonucleotides of 22-mer containing nucleic acid sequences located at 5' and 3'-ends of the 'D12-900' of claim 1, respectively, and being capable of identifying cultivar of hybrids of 'Dongrae Koryogi' zoysia grass.

* * * * *

SEQUENCE LISTING

<160> NUMBER OF SEQ ID NOS: 3

<210> SEQ ID NO 1
<211> LENGTH: 957
<212> TYPE: DNA
<213> ORGANISM: Artificial Sequence
<220> FEATURE:
<223> OTHER INFORMATION: Dongrae Koryogi specific DNA marker D12-900
      capable of identifying cultivars of hybrids

<400> SEQUENCE: 1

```
caccgtatcc ccaggaaagt tggaaccaag aagtgaaagg ttgctcttca tattgtgggt      60
catgacgatg aacccgaaga gccacaggag atcaacatgg ttttagctaa gcctctagat     120
catgagagag gcagagtgca ctgactatat atggaatgca tcaacagcaa ttgtgagaag     180
aggagataat tgctattcta aggacaagca atgcattgaa actaagtttt ggagtttctt     240
tcatgcagat tattacaact tagtgtacgt ggtgatgaag aatctaatta ttgagatgca     300
gtggacggat taggaataca tggccaagaa gaacaatgca gtattcaatg aagttattga     360
ggcttgcaca tatcatggga ttaaggacat cttagatttc aagtatccat ggaataaagc     420
agttatcgct cagttctatg ccactatcta ttatcatcag aaaagagagg ccaagatttc     480
ttggatgaca ggttcagacg tctactcagt cacagtgaga cgctttgcca atattataaa     540
gttccgcagc ggtttctcca atgaggccag aaatcacaat aagctagtgc ttgatgtcaa     600
tgctatgaat ttcatgtatg aaacctccct cacatttctc tacaccaaac cctactgggt     660
tccttccctt ctatattttt ggctccataa aagttctgta cagtatactt ctagttgact     720
aataaacaaa tgacaggtat ttaacacaaa attattcttg ataatcatag cactttcggt     780
accattttca ttgtccaaga tcacacggtc agcacatgta ctccgtccaa cggataataa     840
ccatgtaatg acttgaaagt attttagttc aattgactca ccaggtttgc acagcgatgc     900
atgtggcggc tggtagtagc attctagatg ataaggttga tcatgcagga tacggtg      957
```

<210> SEQ ID NO 2
<211> LENGTH: 22
<212> TYPE: DNA
<213> ORGANISM: Artificial Sequence
<220> FEATURE:
<223> OTHER INFORMATION: D12F primer; Dongrae Koryogi-specific STS
      marker

<400> SEQUENCE: 2
caccgtatcc ccaggaaagt tg                                              22

<210> SEQ ID NO 3
<211> LENGTH: 22
<212> TYPE: DNA
<213> ORGANISM: Artificial Sequence
<220> FEATURE:
<223> OTHER INFORMATION: D12R primer; Dongrae Koryogi-specific STS
      marker

<400> SEQUENCE: 3
caccgtatcc tgcatgatca ac                                              22